US010576392B2

(12) United States Patent
Steffens et al.

(10) Patent No.: US 10,576,392 B2
(45) Date of Patent: Mar. 3, 2020

(54) DISTILLATION COLUMN AND USE THEREOF FOR CLEANING ISOCYANATES

(71) Applicant: COVESTRO DEUTSCHLAND AG, Leverkusen (DE)

(72) Inventors: Friedhelm Steffens, Leverkusen (DE); Wilfried Hedderich, Hilden (DE); Jürgen Bausa, Kürten (DE); Franz Beggel, Köln (DE); Volker Michele, Köln (DE)

(73) Assignee: Covestro Deutschland AG, Leverkusen (DE)

( * ) Notice: Subject to any disclaimer, the term of this patent is extended or adjusted under 35 U.S.C. 154(b) by 0 days.

(21) Appl. No.: 15/772,543

(22) PCT Filed: Sep. 23, 2016

(86) PCT No.: PCT/EP2016/072666
§ 371 (c)(1),
(2) Date: May 1, 2018

(87) PCT Pub. No.: WO2017/076551
PCT Pub. Date: May 11, 2017

(65) Prior Publication Data
US 2018/0318728 A1 Nov. 8, 2018

(30) Foreign Application Priority Data
Nov. 2, 2015 (EP) .................................... 15192510

(51) Int. Cl.
*B01D 3/14* (2006.01)
*C07C 263/20* (2006.01)
*B01D 3/32* (2006.01)

(52) U.S. Cl.
CPC .............. *B01D 3/141* (2013.01); *B01D 3/32* (2013.01); *C07C 263/20* (2013.01)

(58) Field of Classification Search
CPC .......... B01D 3/141; B01D 3/32; C07C 263/20
See application file for complete search history.

(56) References Cited

U.S. PATENT DOCUMENTS

| 3,412,016 | A | * | 11/1968 | Graven | .................. | B01D 3/141 |
| | | | | | | 196/102 |
| 4,847,408 | A | | 7/1989 | Frosch et al. | | |
| 5,136,087 | A | | 8/1992 | Van Horn et al. | | |
| 5,449,818 | A | | 9/1995 | Biskup et al. | | |
| 5,925,783 | A | | 7/1999 | Jost et al. | | |
| 6,218,439 | B1 | | 4/2001 | Kobayashi et al. | | |
| 7,118,653 | B2 | * | 10/2006 | Brady | .................. | C07C 263/20 |
| | | | | | | 203/29 |
| 7,592,479 | B2 | | 9/2009 | Stroefer et al. | | |
| 8,088,944 | B2 | * | 1/2012 | Woelfert | ................ | B01D 3/141 |
| | | | | | | 560/347 |
| 8,901,346 | B2 | | 12/2014 | Merenov et al. | | |
| 9,035,087 | B2 | | 5/2015 | Maeba et al. | | |
| 9,796,669 | B2 | | 10/2017 | Knauf et al. | | |
| 2003/0047438 | A1 | | 3/2003 | Tamura et al. | | |
| 2004/0118672 | A1 | | 6/2004 | Grün et al. | | |
| 2008/0251127 | A1 | | 10/2008 | Zuber et al. | | |
| 2010/0298596 | A1 | | 11/2010 | Keggenhoff et al. | | |
| 2011/0178328 | A1 | | 7/2011 | Merenov et al. | | |
| 2015/0122630 | A1 | | 5/2015 | Lee et al. | | |

OTHER PUBLICATIONS

Chemical Engineering and Processing, 49 (2010), 139-146.
Chemical Engineering, Aug. 2014, 40-48.
Chr. Hiller, Auslegung von Trennwandkolonnen: Modellierungsansätze und experimentelle Validierung, Chapter 2 of the lecture notes of the dividing wall column symposium of Oct. 13, 2011 at the Institute for Process and Plant Technology of the Technical University of Hamburg-Harburg.
G. Niggemann et al., Ind. Eng. Res. 2010, 49, 6566-6577.
Chr. Hiller et al., Heat Mass Transfer (2010) 46, 1209-1220.
Chemineer Tech News, Kenics Statik-Mischer, Chemineer Ltd., 1994.
Sulzer Chemtech, Misch-und Reaktionstechnik.

\* cited by examiner

*Primary Examiner* — Paul A Zucker
(74) *Attorney, Agent, or Firm* — Donald R. Palladino

(57) ABSTRACT

A distillation column for separating a multicomponent mixture into at least three fractions. The distillation column has at least one separating wall and at least one material exchange element (1) above the at least one separating wall. A device (10) for mixing the steam flows flowing upwards to the left and the right of the at least one separating wall is arranged between the at least one separating wall and the at least one material exchange element (1). The use of the distillation column for purifying isocyanates, in particular for toluene diisocyanate (TDI), is also described.

22 Claims, 9 Drawing Sheets

DISTILLATION COLUMN AND USE THEREOF FOR CLEANING ISOCYANATES

CROSS-REFERENCE TO RELATED APPLICATIONS

This application is a national stage application under 35 U.S.C. § 371 of PCT/EP2016/072666, filed Sep. 23, 2016, which claims the benefit of European Application No. 15192510.4, filed Nov. 2, 2015, both of which are being incorporated by reference herein.

FIELD

The present invention is concerned with a distillation column for fractionating a multi-component mixture into at least 3 fractions, wherein the distillation column comprises at least one dividing wall and above the at least one dividing wall comprises at least one mass transfer element (1), wherein between the at least one dividing wall and the at least one mass transfer element (1) an apparatus (10) for mixing the vapor streams ascending left and right of the at least one dividing wall is arranged. The present invention is likewise concerned with the use of the distillation column according to the invention in the purification of isocyanates, in particular in the purification of tolylene diisocyanate (TDI).

BACKGROUND

If a substance mixture consisting of at least one low-boiling component (A), a medium-boiling component (B) and a high-boiling component (C) is to be separated by distillation the use of simple distillation columns without a dividing wall general necessitates two distillation columns; cf. *Chemical Engineering and Processing*, 49 (2010), 139-146. In this way in the first distillation column K1 (cf. FIG. 1) the low boiler (A) may be removed overhead. In the column bottom a bottoms product free from low boilers is achieved which may then be further fractionated in a second column K2. The medium boiling component (B) is obtained at the column top and the high boiling component (C) at the column bottom. According to the composition of the mixture to be separated and the separability of the individual components (i.e. their differences in boiling point) the high boiler (C) may also initially be removed at the column bottom of the first column K1 (cf. FIG. 2). The mixture of low boilers and middle boilers (A, B) obtained at the column top is then fractionated in the second column K2. The low-boiling component (A) is obtained at the column top and the middle boiling component (B) at the column bottom.

In many cases the use of a distillation column having at least one dividing wall (hereinbelow dividing wall column) is in terms of capital and energy costs the more economic alternative to the classical separation sequence. With a dividing wall column all components may be separated in one step (cf. FIG. 3). This is made possible by a dividing wall arranged in the middle portion of the column. The mixture to be separated, also referred to as feed, must be added on the opposite side to the product withdrawal for the middle-boiling component. FIG. 4 shows a typical arrangement of the mass transfer elements, structured packings very often being employed. Arranged above the dividing wall (2) is a common mass transfer element (also referred to as a packing bed) (1). It serves for enrichment of the low-boiling component (A) by removal of the medium-boiling component (B). Arranged left and right of the dividing wall are the mass transfer elements (packing beds) 4, 41, 3 and 31. Bed 4 and 31 serve for removal of the low-boiling component (A) so that this component can reach neither the sidestream withdrawal for the middle boiling component (B) nor the region below the dividing wall. Bed 3 and 41 serve for removal of the high-boiling component (C) with the aim of being ideally free of component (C) in the region above the dividing wall and at the sidestream withdrawal for the component (B). The common bed 10 serves for concentration of the high-boiling component (C).

As intimated in *Chemical Engineering*, August 2014, 40-48 the importance of dividing wall columns has steadily increased since about 1985 and today encompasses not only asymmetrically arranged dividing walls but also applications with more than one dividing wall. For further energy integration intermediate evaporators and/or condensers are possible, as described in WO 2010/039972 A2. This application further describes cf. FIG. 1—the arrangement of two internals (124, 122—"trays") in the region above the dividing wall. Located between these two internals is a product outlet (128). Both internals are located in a region of the dividing wall column in which ascending vapor and downward-trickling liquid move in countercurrent; thus mass transfer elements and not apparatuses for homogenizing pure vapor streams are concerned.

EP 1 980 303 A2 is concerned with a special reflux divider (2) for dividing wall columns (1). The reflux divider (2) is arranged outside the column (1) (cf. FIG. 1). The document discloses two embodiments of the reflux divider (2); cf. FIG. 2a and FIG. 2b. In both embodiments the column (1) comprises above the dividing wall a liquid collector (13) which comprises a tray (15) and chimneys (16). The document does not disclose that in the region between the end of the dividing wall and the packing (12) a particular homogenization of the ascending vapor takes place. Ascending vapor cannot become commixed in chimneys since the purpose of these is to minimize pressure drop by provision of a high free cross section.

US 2003/0047438 A1 is concerned with special dividing wall columns. FIGS. 1 and 21 show via apparatus (54) and laminas (71) a liquid collector. The mode of action of this liquid collector is described in paragraph [0052]. It is said therein that the ascending vapors are deflected from the column center but nevertheless a sufficient contact of liquid and vapor is ensured in the adjacent mass transfer elements. An apparatus for homogenization of ascending vapor stream is between the upper edge of the dividing wall and a mass transfer element is not disclosed in this document. Laminar liquid collectors as described in this document (cf. 54 and 71 in FIG. 3) are not suitable for homogenization of vapor stream in columns.

EP 2 829 308 A2 is concerned with a liquid distributor (100) for dividing wall columns. FIG. 1 shows the devices in such a liquid distributor inside a dividing wall column directly above the dividing wall (190). Shown as devices in the liquid distributor are inter alia a liquid collector (130) implemented as a chimney tray (134, 136). Due to the multiplicity of chimneys the described liquid collector is unsuitable for commixing of ascending vapor streams.

The manifold possibilities make dividing wall column technology an important component for reducing energy consumption and manufacturing costs in production.

A typical application of dividing wall column technology is purification of isocyanates, in particular tolylene diisocyanate (hereinbelow TDI). Here, in the chemical reaction of the relevant amine (in particular tolylene diamine, hereinbelow TDA) with phosgene using an inert solvent either as a diluent during the reaction and/or as a quenching medium for rapid reaction termination, a crude product is obtained which must then be worked up by distillation. In the case of TDI (cf. EP 1 371 635 B1 and EP 1 413 571 B1) the dividing wall column is generally utilized for separating the TDI from low-boiling components, from the solvent and high-boiling components in order to obtain it as a saleable product. Thus EP 1 371 635 B1 describes a dividing wall column with less than 2% of the low-boiling component phosgene in the feed. The product stream is withdrawn from EP 1 371 635 B1 in the region of the dividing wall, on the side facing away from the feed, with a purity of at least 99.5 wt %. Said stream contains less than 200 ppmw of solvent and/or chlorinated aromatic hydrocarbons, less than 100 ppmw of hydrolyzable chlorine (HC) and less than 40 ppmw of acidic fractions. Generated at the column bottom is a material stream enriched in high-boiling components. EP 1 413 571 B1 describes a process for purifying TDI in which the feed mixture to the dividing wall column contains less than 20 wt % of solvent. This solvent is withdrawn at the top of the column with a purity of 20 to 99 wt % and contains all low-boiling components. The requirements concerning the purity of the TDI product stream is described analogously to that in EP 1 371 635 B1. EP 1 575 907 B1 describes a process for purifying TDI in combination with a further concentration of the higher boiling components. The TDI fraction generated in the concentration of the higher boiling components is sent back to the dividing wall column for recovery. As a consequence thereof this dividing wall column has 2, optionally 3 feeds and depending on the arrangement a dividing wall which runs right into the column bottom.

Since the obtained TDI is generally the commercial product high demands for maintaining quality are placed on it. Any malfunction of the dividing wall column results in off-specification product. The other stream obtained must also achieve the required specifications in terms of their composition since they are often recycled into the production process for reuse. If the specifications are not achieved this can result in inefficiently high circuit streams or in yield losses, in particular when for example in the case of the production of isocyanates and in particular TDI the recovered solvent does not achieve the required purity for use in the reaction stage. This places high demands on the dimensioning of the column and on the fabrication thereof.

The dimensioning of dividing wall columns is generally effected through stationary simulators, such as are commercially available for example from AspenTech. The simulation may generally be effected by interconnection of conventional columns (cf. Chr. Hiller "*Auslegung von Trennwandkolonnen: Modellierungsansätze and experimentelle Validierung*", Chapter 2 of the lecture notes of the dividing wall column symposium of Oct. 13, 2011 at the Institute for Process and Plant Technology of the Technical University of Hamburg-Harburg). FIG. 5 shows such an arrangement. Column 1 (K-1) represents the portion above the dividing wall. The region of the dividing wall is depicted by two further, separate columns (K-2, K-3). K-4 mirrors the region below the dividing wall. The apparatuses belonging to the column such as condensers and evaporators are advantageously described as separate models but may also be integrated into the column models K-1 and K-4 depending on the simulation program used. Through connecting material streams the individual columns K-1 to K-4, the condenser and the evaporator become one dividing wall column. As column models equilibrium step models or else non-equilibrium step models may be employed. Equilibrium state models are the simpler and more flexible approach here since they require fewer material data. However, these models reach their limits for strongly non-ideal material systems.

Essential for the fitness for purpose of a dividing wall column is the division of the vapors from the lower common portion K-4 between the two sides of the dividing wall K-2 and K-3. This division is only dependent on the ratio of the pressure drops left and right of the dividing wall. In real columns the pressure drop depends on the chosen column internals and on gas and liquid load. For simulation as a basis for dimensioning it is thus necessary to use process models able to calculate pressure drop as a function of the hydrodynamics of the column internals used later. Only then is an assured forecast of the separation performance of the column, especially for partial load behavior and altered operating parameters such as alteration of the composition of the feed, possible.

The validity of the simulation should be verified by experimental data, particularly when the description of the material data cannot be achieved with the required precision or else product properties not applicable to a simulation (for example color) must be achieved. Studies (cf. G. Niggemann et al., *Ind. Eng. Res.* 2010, 49, 6566-6577) revealed good agreement between laboratory and simulation results, in particular with respect to the gas distribution below the dividing wall. The test setup consists of a distillation column having an internal diameter of 68 mm and containing a plurality of Montz B1-500 mass transfer elements. In addition to the good agreement of experimental and calculated results this publication reports on the influence of heat transport on the separator behavior of the column. However, this influence is limited to laboratory columns since relative to throughput the surface area of the dividing wall is much greater here than for industrial columns Another paper (Chr. Hiller et al., Heat Mass Transfer (2010) 46, 1209-1220) also confirms good agreement of experimental data with the simulation results using non-equilibrium models.

For industrial implementation of dividing wall columns various manufacturers (for example Sulzer Chemtech, Montz) market the relevant column internals such as liquid collectors and redistributors. The dividing wall may either be welded to the outer column jacket or else loosely inserted, as described in EP 1 008 577 A1.

In conclusion it should be noted that the configuration of dividing wall columns for large industrial scale applications is typically based on simulations whose agreement with experimental data is generally regarded as sufficient. However, in operational practice it has been found that, surprisingly, this is not always the case. It was thus observed that for instance the purity of TDI withdrawn as a sidestream in the region of the dividing wall can in reality occasionally deviate significantly from the purity to be expected from simulation results. The same applies to the purity of the solvent withdrawn as a low-boiling component at the top of the dividing wall column. There was therefore a need for further improvements to existing dividing wall columns.

SUMMARY

Taking account of this need the present invention provides a distillation column for fractionating a multi-component mixture into at least 3 fractions, wherein the distillation column comprises at least one dividing wall (2) and above the at least one dividing wall comprises at least one mass transfer element (1), wherein between the at least one dividing wall (2) and the at least one mass transfer element (1), in case of the presence of a plurality of mass transfer elements (1) between the at least one dividing wall (2) and the lowest mass transfer element (1), an apparatus (10) for mixing the vapor streams ascending left and right of the at least one dividing wall is arranged.

The present invention further provides for the use of the distillation column according to the invention for purifying isocyanates, in particular for purifying tolylene diisocyanate (TDI). In other words the present invention further provides for a process for purifying isocyanates, in particular for purifying tolylene diisocyanate (TDI), in which a distillation column according to the invention is employed.

BRIEF DESCRIPTION OF THE SEVERAL VIEWS OF THE DRAWINGS

FIG. 8b is a cross section of a mixing apparatus depicted by FIG. 8a;

FIG. 8c is a photograph of a mixing apparatus depicted by FIG. 8a;

FIGS. 9b and 9c are cross sections of a mixing apparatus depicted in FIG. 9a;

FIG. 10c is a cross section of the sloping baffle plates depicted in FIG. 10a

FIG. 12c is a cross section of the sloping baffle plates depicted in FIG. 12a;

FIG. 14b is a cross section of the tubes depicted in FIG. 14a.

DETAILED DESCRIPTION

Figure 1:
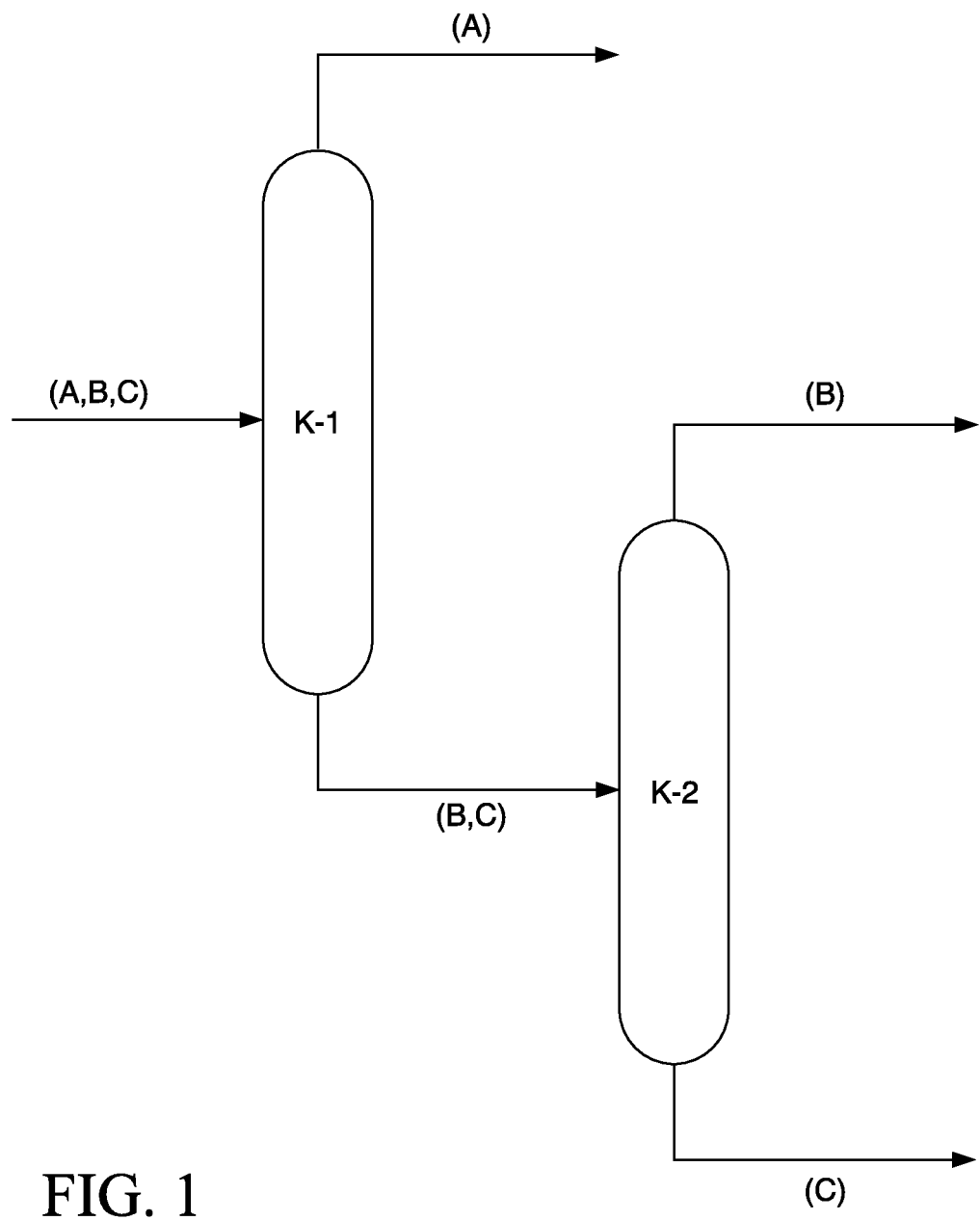
FIG. 1 is a schematic illustration of two distillation columns arranged to separate by distillation a mixture consisting of at least one low-boiling component, a medium-boiling component and a high-boiling component.
Figure 2:
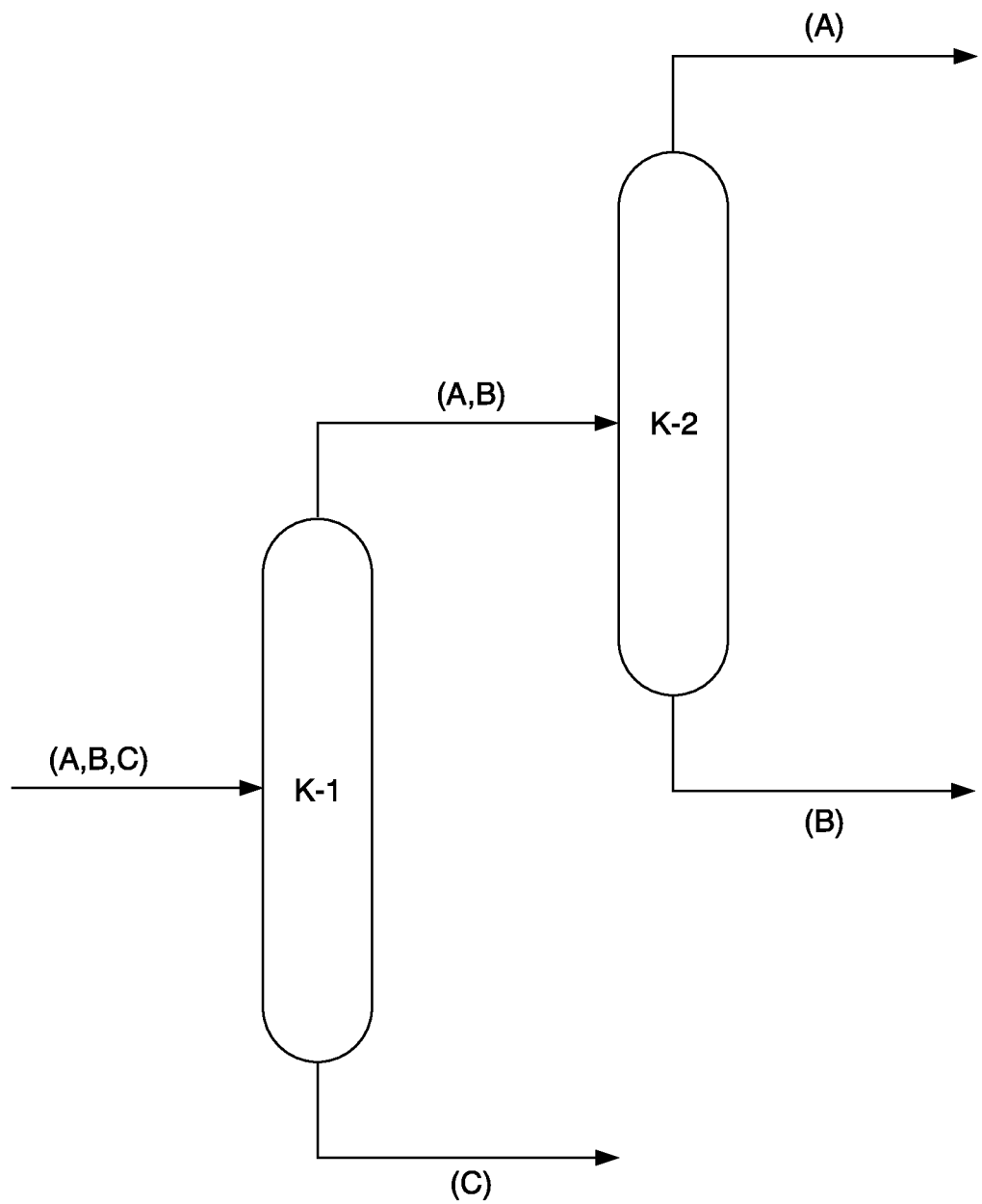
FIG. 2 is a schematic illustration of a variation of the arrangement depicted in FIG. 1, wherein the high-boiling component is initially removed at the column bottom of the first column.
Figure 3:
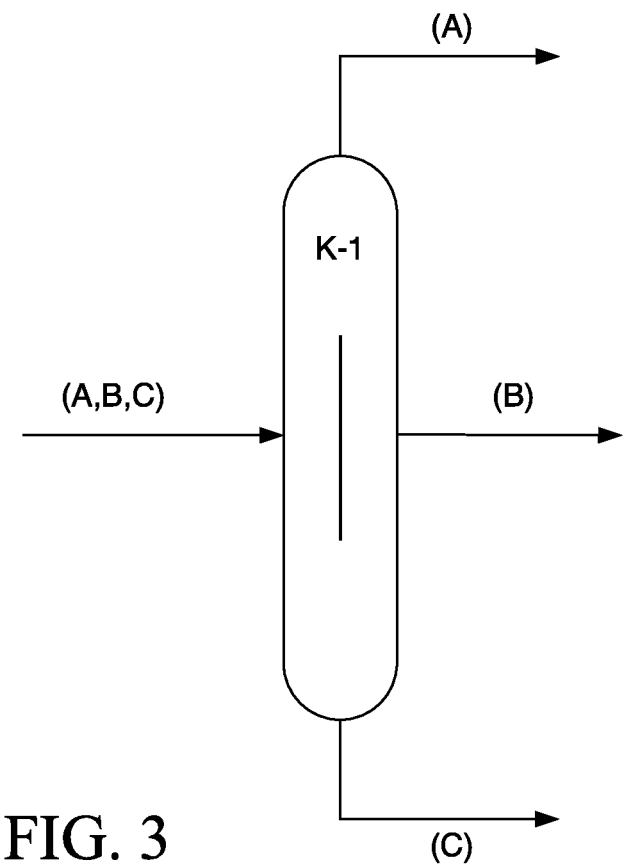
FIG. 3 is a schematic illustration of the use of a distillation column having a dividing wall arranged in the middle portion of the column.

According to the invention the distillation column comprises at least one dividing wall (2), a dividing wall column is thus concerned. The at least one dividing wall is arranged vertically in the interior of the distillation column. The distillation column according to the invention preferably comprises not more than 2 dividing walls, very particularly preferably 1 (i.e. precisely one) dividing wall. In case of more than one dividing wall the dividing walls are arranged side by side with respect to the longitudinal axis of the column body and may have different heights. It is preferable but not compulsory when the at least one dividing wall is arranged symmetrically, i.e. in case of a single dividing wall said dividing wall is located in the middle of the cross section of the column body. In case of a plurality of dividing walls the wording "vapor streams ascending left and right of the at least one dividing wall" relates to the relevant vapor streams of all dividing walls present.

Located above the at least one dividing wall (2) is at least one mass transfer element (1). If a plurality of dividing walls of different heights are present the at least one mass transfer element (1) is located above the highest dividing wall. The distillation column according to the invention preferably comprises not more than 2 mass transfer elements above the at least one dividing wall, very particularly preferably 1 (i.e. precisely one) mass-transfer column (1) above the at least one dividing wall. If a plurality of mass transfer elements (1) are present these are arranged one above the another. It is preferable when the at least one mass transfer element (1), in case of the presence of a plurality of mass transfer elements (1) at least the lowest mass transfer element (1), extends over the entire cross section of the column body. In the at least one mass transfer element (1) above the dividing wall region a mass transfer between ascending vapor and descending liquid takes place. The at least one mass transfer element (1) is thus located in a region of the distillation column in which vapor and liquid phases collide in countercurrent (in contrast to the mixing apparatus (10) as more particularly elucidated hereinbelow).

According to the invention there is located between the at least one dividing wall and the at least one mass transfer element (1) an apparatus (10) for mixing the vapor streams ascending left and right of the at least one dividing wall. In the context of the invention this apparatus (10) may comprise static and/or movable mixing elements as more particularly elucidated hereinbelow. This mixing apparatus (10) is located in a region of the distillation column in which the vapor streams from the region of the at least one dividing wall (2) ascend without colliding with descending liquid. The mixing apparatus (10) therefore brings about a homogenization of the vapor streams without mass transfer.

It has been found that, surprisingly, the problems reported above in connection with the purity of the product streams may be solved or at least ameliorated by installation of such an apparatus. Without wishing to be bound to any particular theory it is believed that without such an apparatus in dividing wall columns having at least one mass transfer element above the dividing wall (the mass transfer element (1)) the commixing of the vapor streams ascending from the dividing wall region on the left and on the right is non-ideal. This non-ideal commixing leads to an incoming flow to the mass transfer element above the dividing wall which is nonuniform in terms of vapor velocity and vapor composition and accordingly to a loss of separation performance. This commixing of the vapor streams becomes all the worse, the greater the column diameter. This is due to the available height between the upper edge of the dividing wall and the mass transfer element located thereabove which in relative terms becomes progressively smaller with increasing column diameter. The present invention therefore makes possible a homogenization of the vapor streams (also referred to as vapors for short) after exiting from the dividing wall region and before entering into the first mass transfer element above the dividing wall region (i.e. that referred to in the terminology of this invention as mass transfer element (1)). This homogenization increases the separation performance of the column and the product specifications upon which the dimensioning of the column is based may therefore be satisfied again.

The invention in general and various embodiments of the invention in particular are more particularly described hereinbelow with reference to the figures. Various embodiments may be combined with one another as desired, unless the opposite is apparent to the person skilled in the art from the overall technical context.

Figure 6:
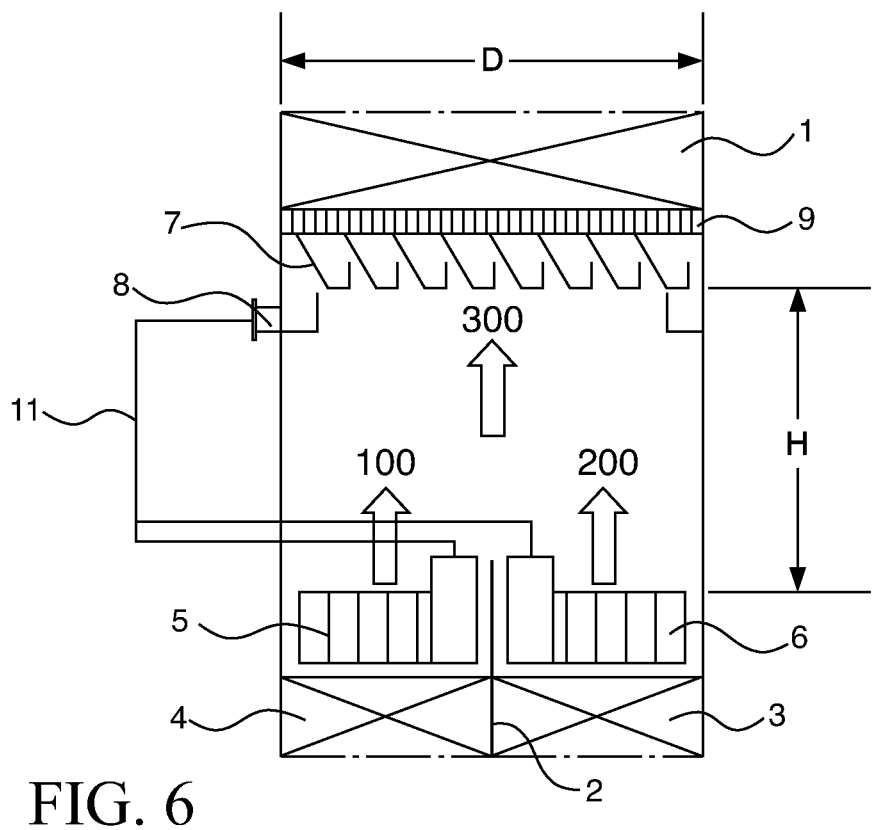
FIG. 6 is an elevation view of the region between the upper end of the dividing wall and the next highest mass transfer element in a conventional distillation column.

FIG. 6 shows the region between the upper end of the dividing wall (2) and the next highest mass transfer element (1) in a conventional distillation column without the inventive apparatus for homogenizing the vapor streams (10). Located at the upper end of the dividing wall (2) are the mass transfer elements (3) and (4) and the accompanying liquid distributors (5) and (6) in each case left and right of the dividing wall. The mass transfer element (1) rests on a supporting grid (9). The liquid effluxing from the mass transfer element (1) is collected for redistribution by a liquid collector (7) and transferred into the annular channel (8) having exit stubs and from there applied via conduits (11) located outside the column body to the liquid distributors (5) and (6). The vapor streams $m_L$ (100) and $m_R$ (200) exit from the dividing wall region on the left and on the right with the velocities $w_L$ and $w_R$ and the concentrations $x_L$ and $x_R$. To achieve the maximum separation performance in the mass transfer element (1) a homogenization of these vapor streams is necessary with the aim of achieving a mixed overall stream $m_G$ (300) having a mixed concentration $x_m$ and a uniform vapor velocity $w_m$ over the entire cross section of the column before entry into the mass transfer element (1). The height H is available therefor.

According to the invention for achieving this aim the apparatus (10) for mixing the vapor streams ascending left and right of the at least one dividing wall is used. The purpose of this mixing apparatus (10) is a homogenization of the ascending vapor streams before these come into contact with descending liquid in the region of the at least one mass transfer element (1). The mixing apparatus (10) is therefore located in a region of the distillation column where no descending liquid from the upper region of the distillation column appears. Such a region is preferably realized in terms of apparatus when in the distillation column according to the invention below the at least one mass transfer element (1), in case of the presence of a plurality of mass transfer elements (1) below the lowest mass transfer element (1), a liquid collector (7) for collecting the liquid effluxing from the at least one mass transfer element (1) is arranged. This liquid collector (7) is configured such that the liquid collected in said collector is passed into the region of the at least one dividing wall (2), i.e. in particular is applied to liquid distributors (5) and (6) arranged in the region of the at least one dividing wall (2), such that in the region between the at least one dividing wall (2) and the at least one mass transfer element (1), in case of the presence of a plurality of mass transfer elements (1) between the at least one dividing wall (2) and the lowest mass transfer element (1), no descending liquid from the upper region of the distillation column appears. It is preferable when to this end the liquid collected in the liquid collector (7) is transferred into an annular channel arranged below the liquid collector (7).

Figure 7:
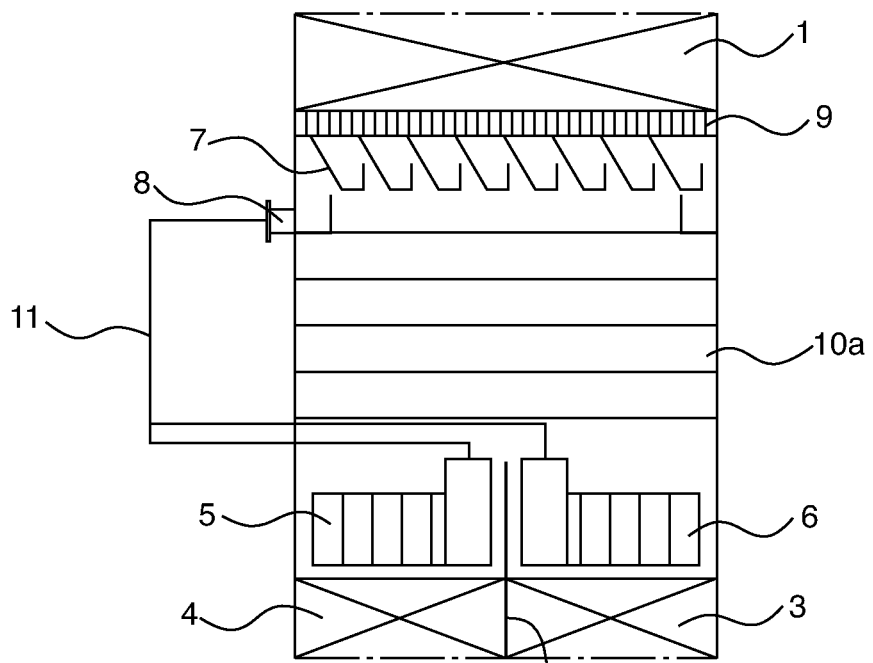
FIG. 7 is an elevation view of a distillation column that includes a mixing apparatus according to some embodiments of the present invention, in which the mixing apparatus is a mixer packing.

In the distillation column shown in FIG. 6 such a region without descending liquid is located above the dividing wall (2) and below the annular channel (8). In this region the mixing apparatus (10) according to the invention is preferably installed as shown in FIG. 7 with the example of a mixer packing (10a). The condition that in this region no descending liquid comes into contact with the ascending vapor is achieved in the embodiment shown in FIG. 7 by a configuration of the distillation column according to the invention such that arranged below the mass transfer element (1) is a liquid collector (7) for collecting the liquid effluxing from the at least one mass transfer element (1), wherein the liquid collector (7) is in turn configured such that the liquid collected therein is transferred into an annular channel (8) arranged below the liquid collector (7) and from there via an exit stub out from the inside of the distillation column via conduits (11) located outside the column body is applied to liquid distributors (5) and (6) arranged in the region of the at least one dividing wall (2). It will be appreciated that this configuration of the distillation column is not limited to mixer packings (10a) but is also applicable to other mixing apparatuses (10) such as are more particularly elucidated hereinbelow. Said configuration is also applicable to distillation columns having a plurality of mass transfer elements (1) above the at least one dividing wall (2). It is moreover also possible to install the conduits for discharging the liquid from the annular channel (8) inside the distillation column. When in this embodiment the at least one mass transfer element (1) shall extend over the entire cross section of the distillation column, which as previously mentioned is in principle preferable, the at least one mass transfer element (1) is provided with recesses for the conduits for discharging the liquid from the annular channel (8). However, the arrangement shown in FIG. 7 having external conduits (11) is preferred because this does not hinder the installation of the mixing apparatus (10). In addition in this embodiment with external conduits (11) the targeted distribution of the liquid to the liquid distributors (5) and (6) is easier to realize.

Figure 8A:
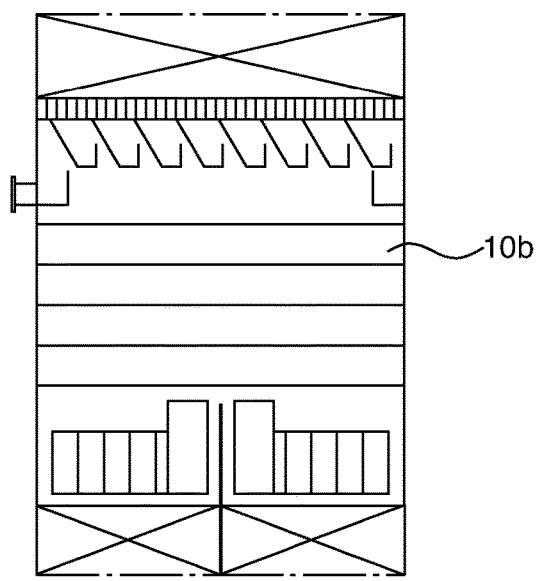
FIG. 8a is an elevation view of a distillation column that includes a mixing apparatus according to some embodiments of the present invention, in which the mixing apparatus is corrugated sheet layers.
Figure 8B:
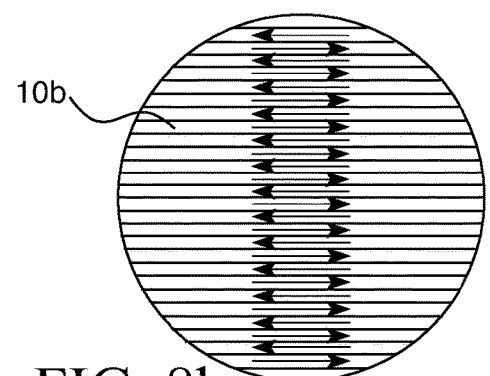
Figure 8C:
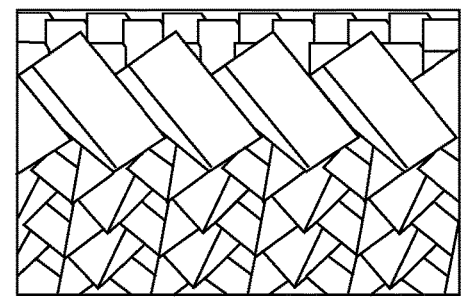

In the context of the invention suitable mixing apparatuses (10) initially include all commercially available gas mixing elements, for example static mixers such as are marketed by various firms and for example described in Chemineer TECH NEWS, *Kenics Statik-Mischer*, Chemineer Ltd., 1994 and SULZER CHEMTECH, *Misch- und Reaktionstechnik*. The previously mentioned mixer packings (10a) are described for example in SULZER CHEMTECH, *Misch-und Reaktionstechnik* (for instance Sulzer mixer packing "SMV/SMVP"; FIG. 7). The mixer packing (10a) may be mounted on a supporting grid similarly to the mass transfer element (1). FIG. 8 shows a mixing element (10b) consisting of corrugated sheet layers—in the embodiment shown without holes, which is preferable—and in contrast to mass transfer elements the individual layers are not twisted. The thus formed channels alternately pass the vapors from left to right and from right to left.

Figure 9A:
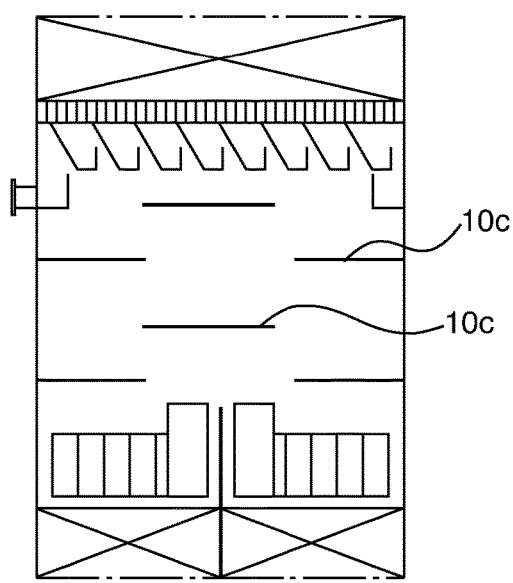
FIG. 9a is an elevation view of a distillation column that includes a mixing apparatus according to some embodiments of the present invention, in which the mixing apparatus is baffle plates.
Figure 9B:
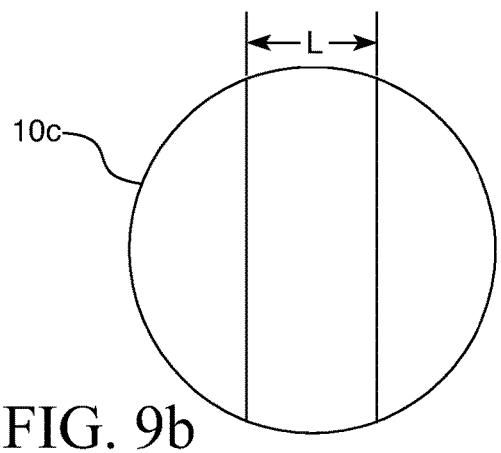
Figure 9C:
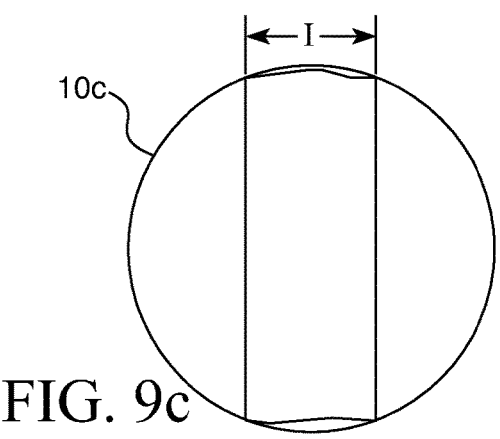
Figure 10A:
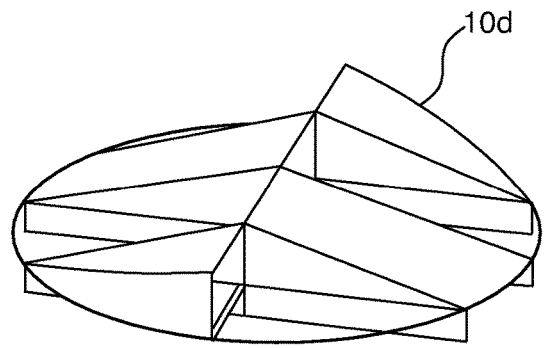
FIG. 10a is a perspective view of baffle plates depicted in FIG. 10b.
Figure 10B:
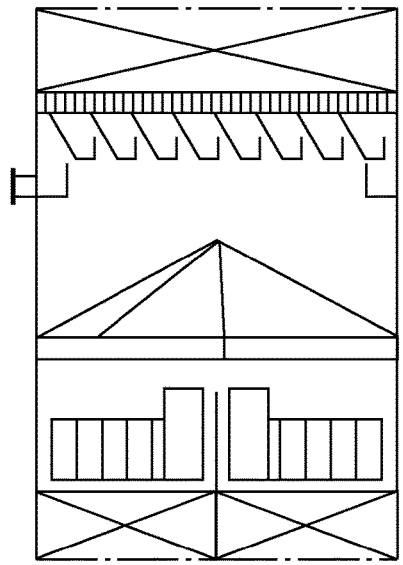
FIG. 10b is an elevation view of a distillation column that includes a mixing apparatus according to some embodiments of the present invention, in which the mixing apparatus is baffle plates having a gradient toward the middle of the column.
Figure 10C:
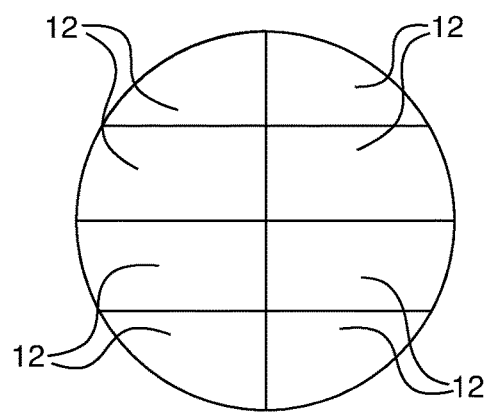

According to the invention the mixing element (10) may also be realized using baffle plates (10c) as shown in FIG. 9. Here, for the values "L" and "1" L=1 is possible, but L may also be smaller or larger than 1. Depending on the mixing task the sheets may also be fully or partially perforated. As shown in FIG. 9, in this arrangement the baffle plates are oriented horizontally. In contrast, baffle plates having a gradient toward the middle of the column are also possible (10d). FIG. 10 shows this option.

Figure 11:
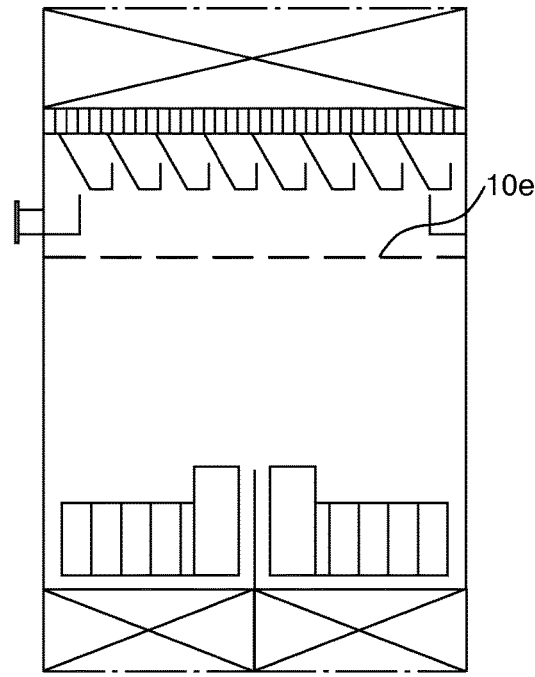
FIG. 11 is an elevation view of a distillation column that includes a mixing apparatus according to some embodiments of the present invention, in which the mixing apparatus is one or more sieve trays.

To ensure the greatest possible uniformity in vapor velocity in the incoming flow to the mass transfer element (1) in the context of the invention one or more sieve trays (10e) may also be employed as per FIG. 11. Alternatively, chimney trays (10f), bubble-cap trays (10g) and valve trays (10h) are suitable internals for homogenizing the vapor velocity.

Figure 12A:
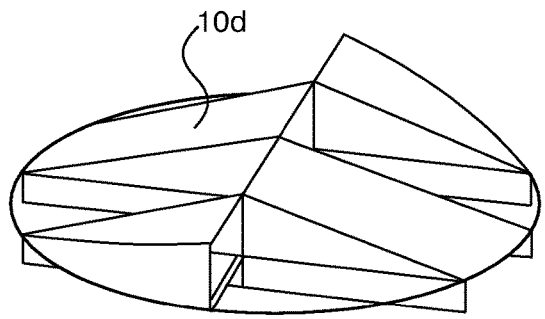
FIG. 12a is a perspective view of sloping baffle plates depicted in FIG. 12b
Figure 12C:
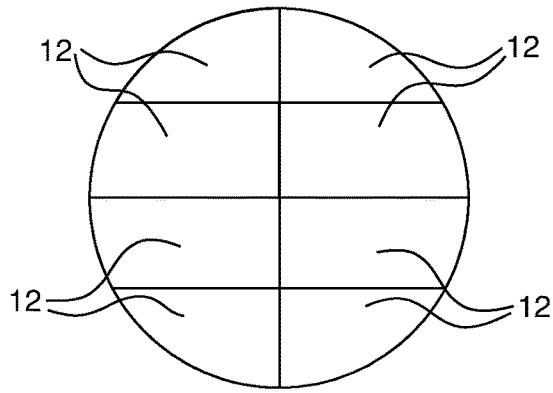
Figure 12B:
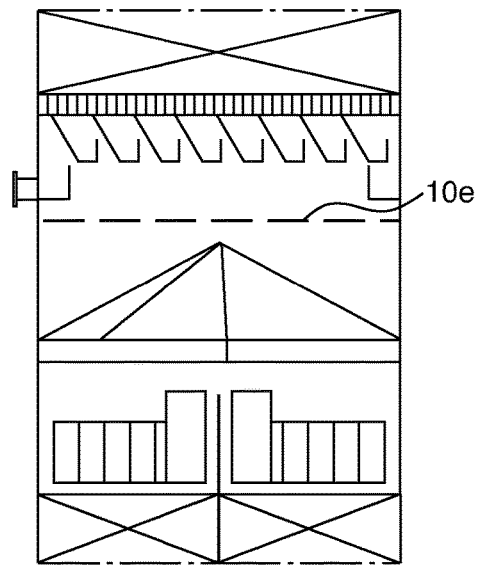
FIG. 12b is an elevation view of a distillation column that includes a mixing apparatus according to some embodiments of the present invention, in which the mixing apparatus is a combination of sloping baffle plates with a sieve tray.

All described collecting elements (10) may also be combined with one another. FIG. 12 shows the combination of sloping baffle plates (10d) for transverse mixing of the vapors with a sieve tray (10e) for homogenizing the vapor velocity. The right-hand part of the figure shows a cross section of the sloping baffle plates 10d shown in the left-hand part of the figure. The white areas (12) are open.

Figure 13A:
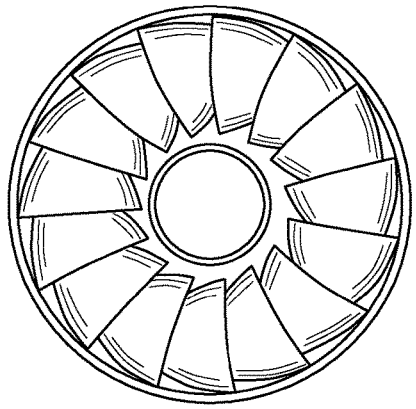
FIG. 13a is a photograph of a stator suitable for use as the mixing apparatus depicted in FIG. 13b.
Figure 13B:
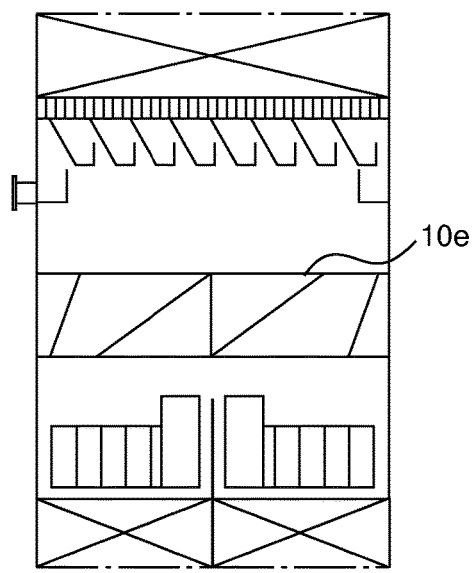
FIG. 13b is an elevation view of a distillation column that includes a mixing apparatus according to some embodiments of the present invention, in which the mixing apparatus is a stator.
Figure 13C:
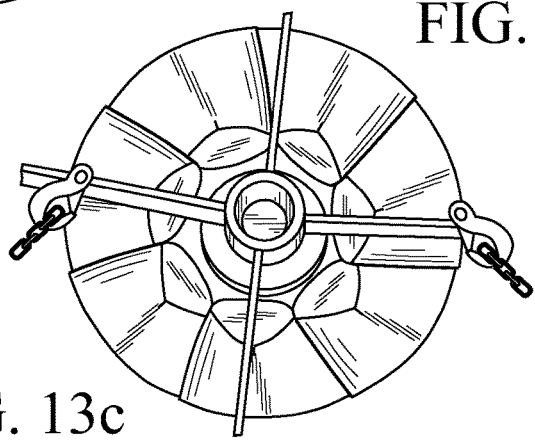
FIG. 13c is a photograph of a stator suitable for use as the mixing apparatus depicted in FIG. 13b.

Stators (10i) are likewise suitable mixing elements (10) in the context of the invention and may be fixed or rotatable. FIG. 13 is a schematic diagram of this solution.

Figure 14A:
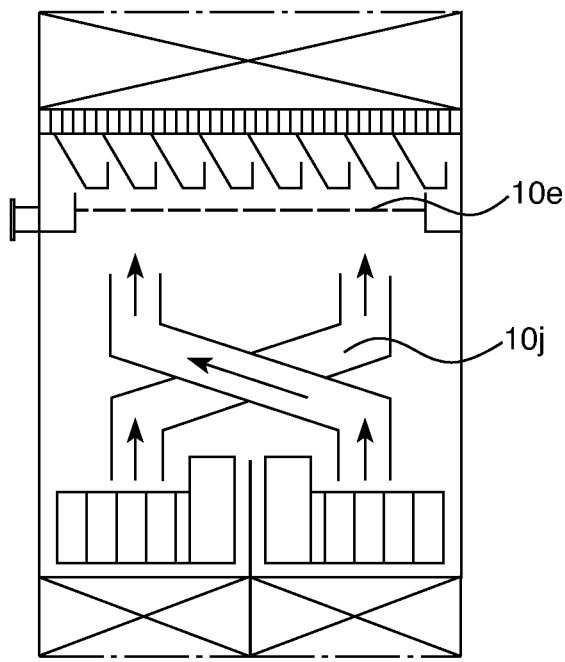
FIG. 14a is an elevation view of a distillation column that includes a mixing apparatus according to some embodiments of the present invention, in which the mixing apparatus is tubes which deflect vapor fractions in combination with a sieve tray.
Figure 14B:
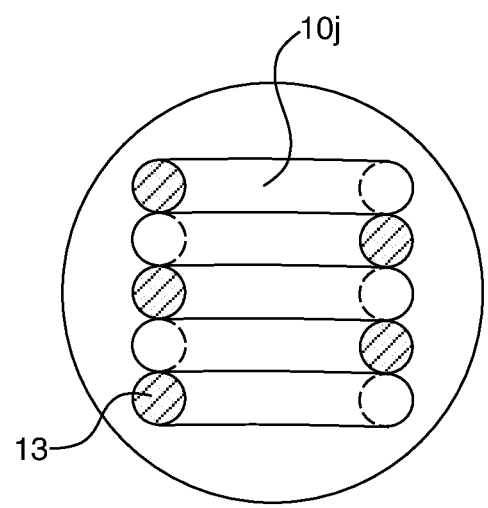

In the context of the invention the commixing of the vapor streams may also be effected via tubes (10j) which deflect vapor fractions from left to right or in the opposite direction. FIG. 14 shows this mixing device (10j) in combination with a sieve tray (10e). The right-hand part of the figure shows a plan view of 10j with an upper vapor exit (13) shown. Instead of tubes (10j) it is also possible to employ channels (10k) of square, rectangular or oval cross section. Channels open at the bottom and having any desired cross section are also suitable for the mixing task in the context of the invention. Likewise suitable are perforated sheets (10l).

Suitable mass transfer elements (1) are known to those skilled in the art. It is preferable to employ dumped packing beds, structured mass transfer packings, bubble-cap trays, valve trays, sieve tays or combinations of the abovementioned apparatuses. In contrast to the mixing apparatus (10) in the region of the mass transfer element (1) vaporous and liquid streams collide in countercurrent; thus a mass transfer between the vapor phase and the liquid phase does in fact take place. By contrast, the mixing apparatus (10) serves only for homogenization of the ascending the vapor stream.

The apparatuses (1) and (10) thus serve different purposes even if they were to be identical in terms of apparatus.

The distillation column according to the invention is in principle suitable for fractionation of any desired multicomponent mixtures (A, B, C) containing at least 3 substances having different boiling points, wherein hereinbelow the component having the lowest boiling point (so-called "low boiler") is referred to as (A), that with the highest boiling point (so-called "high boiler") is referred to as (C) and the component having an intermediate boiling point (so-called "middle boiler") is referred to as (B). The use of the distillation column according to the invention for purifying isocyanates is particularly preferred. This use is more particularly described hereinbelow. It is straightforward for those skilled in the art to transfer the elucidations made there to use in other technical fields.

Figure 4:
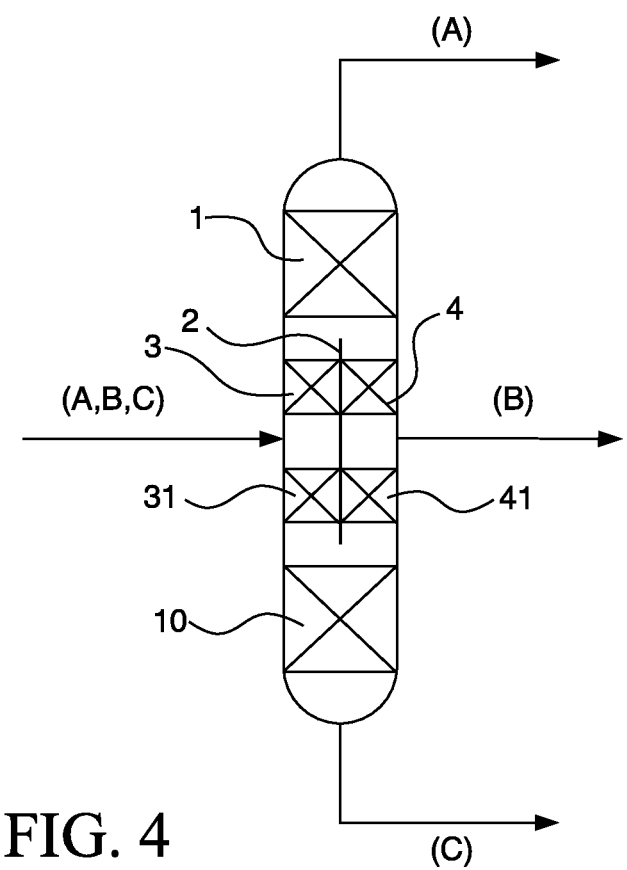
FIG. 4 is a schematic illustration of a typical arrangement of the mass transfer elements such as structured packings often employed in a distillation column having a dividing wall of the type illustrated in FIG. 3.
Figure 5:
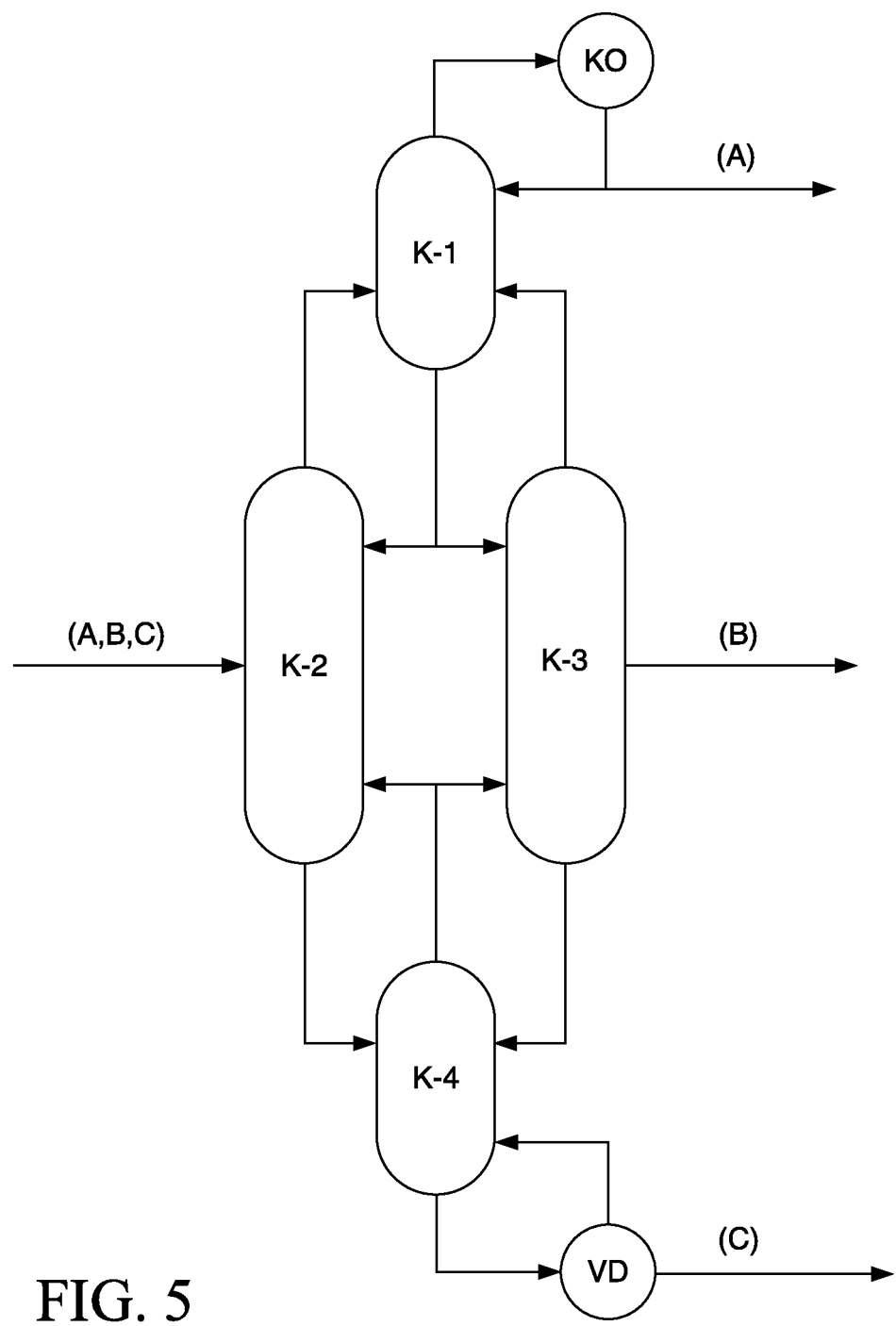
FIG. 5 is a schematic illustration of a simulation effected by interconnection of conventional columns, suitable for use in effecting the dimensioning of a dividing wall column.

The present invention thus further provides for the use of the distillation column according to the invention for purifying isocyanates, in particular for purifying tolylene diisocyanate (TDI). Further suitable isocyanates are methylenediphenyl diisocyanate (MDI), hexamethylene diisocyanate (HDI), pentamethylene diisocyanate (PDI), isophorone diisocyanate (IPDI), m-xylylene diisocyanate (XDI) and dicyclohexylmethane diisocyanate ("H12-MDI"; also known under the trade name "Desmodur W" of Covestro Deutschland AG). The crude isocyanate stream to be purified comprises "low-boiling" fractions (A) such as for example solvents and optionally traces of phosgene and/or hydrogen chloride and "high-boiling" fractions (C) such as polymerized isocyanate fractions. The terms "low-boiling" and "high-boiling" are to be understood in relation to the boiling point of the desired product of value, the isocyanate. This is withdrawn as so-called "middle boiler" (B) in the region of the dividing wall as a sidestream. The "low boilers" (A) are withdrawn from the column as a tops stream and the "high boilers" (C) as a bottoms stream, as shown schematically in FIG. 4 for a conventional dividing wall column (in terms of the withdrawal points inventive dividing wall columns do not differ from conventional ones). The crude diisocyanate stream may originate from any desired process for producing isocyanates from the prior art. WO 2015/144658 (A1), EP 0792 263 (B1), EP 0 570 799 (B1) and EP 0 289 840 (B1) may be mentioned by way of example.

The crude isocyanate stream to be introduced into the distillation column according to the invention is preferably one from which the bulk of the solvent, phosgene and hydrogen chloride has already been removed in upstream purification stages. Such upstream purification stages are known from the prior art and for example described in EP 1 546 091 (B1), U.S. Pat. No. 5,136,087, EP 1 854 783 (A2) and EP 2 210 873 (A1). The distillation column according to the invention is particularly suitable for removal of polymeric isocyanate fractions and fine purification of the desired isocyanate in one step (in particular in the case of TDI). However, said column is also suitable for isomer separation (in particular in the case of fractionation of the individual MDI isomers).

The invention accordingly provides a simple solution for the problems particularized at the outset. The invention is also applicable to existing dividing wall columns because the apparatus (10) may also be retrospectively installed. The examples which follow further illustrate the invention.

EXAMPLES

Example 1 (Comparison—Without Apparatus (10))

A crude TDI mixture consisting of 15 wt % of low-boiling components (predominantly ortho-dichlorobenzene solvent, also traces of phosgene and hydrogen chloride), 1 wt % of higher-boiling components (polymerized TDI fractions and secondary components having a boiling point above TDI) and 84 wt % of middle-boiling components (the target product TDI) is fractionated into three streams. The product specifications expected from simulations and laboratory results are:

(A) a tops product having a content of >98 wt % of low-boiling components.

(B) a sidestream comprising <5 ppmw of low-boiling components.

(C) a material stream (bottoms product) comprising <15 wt % of higher boiling components.

In operational practice the separation is effected in a dividing wall column having a diameter of 3200 mm and at a pressure at the top of the column of 70 mbar. In contrast to the simulation and laboratory results a tops product (A) containing 78 wt % of low-boiling components is obtained. The sidestream (B) contains between 5 and 10 ppmw of low-boiling components. The bottoms stream (C) contains between 8 wt % and 15 wt % of higher boiling components.

Example 2 (Inventive—With Apparatus (10))

The deviation observed in example 1 was attributed by special simulation calculations to an insufficient homogenization of the vapor streams at the exit of the dividing wall. The simulation from example 1 was altered such that the apparatus (10) is accounted for. Now at a column top pressure of 70 mbar on-specification sidestreams were obtained. Thus, a tops product (A) containing 98 wt % of low-boiling components is obtained. The sidestream (B) contains only between 1 and 5 ppmw of low-boiling components. The bottoms stream (C) contains up to 15 wt % of higher boiling components.

What is claimed is:

1. A distillation column for fractionating a multi-component mixture into at least 3 fractions, wherein the distillation column comprises at least one dividing wall and above the at least one dividing wall comprises at least one mass transfer element in which mass transfer between ascending vapor and descending liquid takes place, wherein between the at least one dividing wall and the at least one mass transfer element, or in case of the presence of a plurality of mass transfer elements between the at least one dividing wall and the lowest mass transfer element, an apparatus for mixing the vapor streams ascending left and right of the at least one dividing wall is arranged, the mixing apparatus being located in the distillation column at a location where vapor streams from the at least one dividing wall ascend without colliding with descending liquid.

2. The distillation column of claim 1, wherein the apparatus for mixing the vapor streams ascending left and right of the at least one dividing wall is selected from the group consisting of mixer packings, corrugated sheet layers, straight baffle plates, sloping baffle plates, sieve trays, chimney trays, bubble-cap trays, valve trays, stators, tubes, channels, perforated sheets and combinations of the abovementioned apparatuses.

3. The distillation column of claim 1, wherein the at least one mass transfer element arranged above the dividing wall is selected from the group consisting of dumped packing beds, structured mass transfer packings, bubble-cap trays, valve trays, sieve trays or combinations of the abovementioned apparatuses.

4. The distillation column of claim 1, wherein one dividing wall is present.

5. The distillation column of claim 1, wherein one mass transfer element is present.

6. The distillation column of claim 1, wherein the at least one mass transfer element or, in case of the presence of a plurality of mass transfer elements, at least the lowest mass transfer element, extends over the entire cross section of the column body.

7. The distillation column of claim 1, wherein arranged below the mass transfer element or, in case of the presence of a plurality of mass transfer elements, below the lowest mass transfer element, is a liquid collector for collecting the liquid effluxing from the at least one mass transfer element, wherein the liquid collector is configured such that the liquid collected in the liquid collector is passed the upper end of the at least one dividing wall.

8. The distillation column of claim 7, in which the liquid collector is configured such that the liquid collected in the liquid collector is transferred into an annular channel and from there passed the upper end of the at least one dividing wall.

9. The distillation column of claim 1, wherein arranged below the mass transfer element or, in case of the presence of a plurality of mass transfer elements below the lowest mass transfer element, is a liquid collector for collecting the liquid effluxing from the at least one mass transfer element, wherein the liquid collector is configured such that the liquid collected in the liquid collector is transferred into an annular channel and from there via an exit stub out from the inside of the distillation column via conduits located outside the column body to liquid distributors arranged adjacent to the at least one dividing wall.

10. The distillation column of claim 1, where arranged below the mass transfer element or, in case of the presence of a plurality of mass transfer elements below the lowest mass transfer element, is a liquid collector for collecting the liquid effluxing from the at least one mass transfer element, wherein the liquid collector is configured such that the liquid collected in this liquid collector is transferred into an annular channel and from there via conduits located inside the column body to liquid distributors arranged adjacent to the at least one dividing wall.

11. A method of purifying isocyanates comprising introducing a crude isocyanate into the distillation column of claim 1, wherein both fine purification of the isocyanate and removal of polymeric isocyanate fractions are carried out in the distillation column.

12. A method of purifying isocyanates comprising introducing a crude isocyanate into the distillation column of claim 1, wherein fractionation of the isocyanate into various isomers occurs in the distillation column.

13. The method of claim 11, in which the isocyanate is selected from the group consisting of tolylene diisocyanate, methylenediphenyl diisocyanate, hexamethylene diisocyanate, pentamethylene diisocyanate, isophoronediamine diisocyanate, m-xylylene diisocyanate and dicyclohexylmethane diisocyanate.

14. A distillation column for fractionating a multi-component mixture into at least 3 fractions, wherein the distillation column comprises at least one dividing wall and above the at least one dividing wall comprises at least one mass transfer element in which mass transfer between ascending vapor and descending liquid takes place, wherein between the at least one dividing wall and the at least one mass transfer element, or in case of the presence of a plurality of mass transfer elements between the at least one dividing wall and the lowest mass transfer element, an apparatus for mixing the vapor streams ascending left and right of the at least one dividing wall is arranged, the mixing apparatus being located in the distillation column at a location where vapor streams from the at least one dividing wall ascend without colliding with descending liquid, wherein the apparatus for mixing the vapor streams ascending left and right of the at least one dividing wall is selected from the group consisting of mixer packings, corrugated sheet layers, straight baffle plates, sloping baffle plates, sieve trays, chimney trays, bubble-cap trays, valve trays, stators, tubes, channels, perforated sheets and a combination of any two or more thereof, and wherein the at least one mass transfer element arranged above the dividing wall is selected from the group consisting of dumped packing beds, structured mass transfer packings, bubble-cap trays, valve trays, sieve trays, and a combination of any two or more thereof.

15. The distillation column of claim 14, wherein one dividing wall is present and/or wherein one mass transfer element is present.

16. The distillation column of claim 14, wherein the at least one mass transfer element or, in case of the presence of a plurality of mass transfer elements, at least the lowest mass transfer element, extends over the entire cross section of the column body.

17. The distillation column of claim 14, wherein arranged below the mass transfer element or, in case of the presence of a plurality of mass transfer elements, below the lowest mass transfer element, is a liquid collector for collecting the liquid effluxing from the at least one mass transfer element, wherein the liquid collector is configured such that the liquid collected in the liquid collector is passed to the upper end of the at least one dividing wall.

18. The distillation column of claim 17, in which the liquid collector is configured such that the liquid collected in the liquid collector is transferred into an annular channel and from there passed to the upper end of the at least one dividing wall.

19. The distillation column of claim 14, wherein arranged below the mass transfer element or, in case of the presence of a plurality of mass transfer elements below the lowest mass transfer element, is a liquid collector for collecting the liquid effluxing from the at least one mass transfer element, wherein the liquid collector is configured such that the liquid collected in the liquid collector is transferred into an annular channel and from there via an exit stub out from the inside of the distillation column via conduits located outside the column body to liquid distributors arranged adjacent to the at least one dividing wall.

20. The distillation column of claim 14, where arranged below the mass transfer element or, in case of the presence of a plurality of mass transfer elements below the lowest mass transfer element, is a liquid collector for collecting the liquid effluxing from the at least one mass transfer element, wherein the liquid collector is configured such that the liquid collected in this liquid collector is transferred into an annular channel and from there via conduits located inside the column body to liquid distributors arranged adjacent to the at least one dividing wall.

21. A method of purifying isocyanates comprising introducing a crude isocyanate into the distillation column of claim 14, wherein both fine purification of the isocyanate and removal of polymeric isocyanate fractions are carried out in the distillation column.

22. A method of purifying isocyanates comprising introducing a crude isocyanate into the distillation column of claim 14, wherein fractionation of the isocyanate into various isomers occurs in the distillation column.

* * * * *